United States Patent [19]

Buzza

[11] Patent Number: 4,490,234
[45] Date of Patent: Dec. 25, 1984

[54] METHOD FOR MEASURING IONIC CONCENTRATION UTILIZING AN ION-SENSING ELECTRODE

[75] Inventor: Edmund E. Buzza, Fullerton, Calif.

[73] Assignee: Beckman Instruments, Inc., Fullerton, Calif.

[21] Appl. No.: 350,696

[22] Filed: Feb. 22, 1982

[51] Int. Cl.³ ............................................. G01N 27/46
[52] U.S. Cl. ................................... 204/409; 204/415
[58] Field of Search ............... 204/1 P, 195 P, 409, 204/415

[56] References Cited

U.S. PATENT DOCUMENTS

| | | | |
|---|---|---|---|
| 3,505,195 | 4/1970 | Nielsen et al. | 204/415 |
| 3,997,420 | 12/1976 | Buzza | 204/415 |
| 4,003,705 | 1/1977 | Buzza et al. | 204/195 P |
| 4,149,949 | 4/1979 | Buzza et al. | 204/415 |
| 4,170,523 | 10/1979 | Buzza et al. | 204/195 P |
| 4,172,770 | 10/1979 | Semersky et al. | 204/415 |
| 4,209,300 | 6/1980 | Thibault | 204/415 |

Primary Examiner—T. Tung
Attorney, Agent, or Firm—R. J. Steinmeyer; J. E. Vanderburgh; Timothy R. Schulte

[57] ABSTRACT

A method for measuring the concentration of a gas. The method includes circulating an electrolyte solution between an electrode and a gas-permeable, ion-impermeable membrane spaced from said electrode. The ionic concentration is measured after the circulating electrolyte has been stopped.

5 Claims, 2 Drawing Figures

METHOD FOR MEASURING IONIC CONCENTRATION UTILIZING AN ION-SENSING ELECTRODE

BACKGROUND OF THE INVENTION

1. Field of the Invention

The invention relates to the field of chemical analyzers. More particularly, the invention relates to the field of chemical analyzers using electrochemical measuring systems. In still greater particularity, the invention relates to the field of chemical analyzers utilizing ion-sensing electrodes. By way of further characterization, but not by way of limitation thereto, the invention is a method for sensing ion concentration utilizing an ion-sensing electrode having a gas-permeable ion-impermeable membrane in which an electrolyte solution is pumped between the electrode and the membrane.

2. Description of the Related Art

U.S. Pat. Nos. 4,003,705 and 4,170,523 issued to E. E. Buzza et al. and assigned to the assignee of the present invention describe an electrochemical analysis apparatus for measuring both chloride and carbon dioxide in blood. As disclosed in those patents, the carbon dioxide-sensing element includes a renewable electrolyte disposed between a gas-permeable membrane and an ion-sensitive electrode. Gas diffusing through the membrane from a sample substance in a cup on the opposite side of the membrane from the electrode causes a reaction in the renewable electrolyte which is sensed by the ion electrode. The electrical output of this electrode, either as a rate or equilibrium condition, is proportional to the gas diffusing through the membrane.

In the above-mentioned patents, the sensor is located in communication with the cup containing a substrate with zero partial pressure or partial pressure of the gas to be detected equal to that in the renewable electrolyte, both, for instance, being in equilibrium to the atmosphere. When the sample is introduced into the substrate, the gas of interest is released, diffusing through the membrane, and initiating the reaction in the renewable electrolyte. Several factors may influence the rate of this initiation, such as the reproducibility and the time required for introducing the sample, the quality of stirring employed for mixing the sample with the substrate, and the time interval between renewing the electrolyte and introducing the sample.

In a situation, such as a stopped flow-through system, which requires a high throughput, initiation of the rate reaction by the previous method is not possible. The sample liquid must be premixed with acid, thereby releasing the ion of interest before entering the flow cell where the sensor is located. Thus, the addition of sample is not the event which initiates the rate reaction. Also, the premixed sample is purged by a bicarbonate solution of fixed concentration which is also premixed with acid to act as an internal reference. At no time, therefore, is there a solution of zero or partial pressure of $CO_2$ equal to that of the renewable electrolyte in contact with the outside of the membrane. In this system there is no stirring required in the flow cell during the measuring interval because the sample and acid have been premixed.

SUMMARY OF THE INVENTION

The invention is a method for measuring ionic concentration in a flow cell apparatus. A gas produced by the ion diffuses through a membrane to react with an electrolyte solution. The change in the electrolyte solution is measured by an ion-sensing electrode. The sample solution is pumped through the flow cell and stopped at a point adjacent the sensor. The method inculdes pumping the electrolyte solution between the membrane and the electrode until the measurement is to take place. At this point, the electrolyte pumping is stopped and the ionic concentration is measured.

DESCRIPTION OF THE PREFERRED EMBODIMENT

Figure 1:
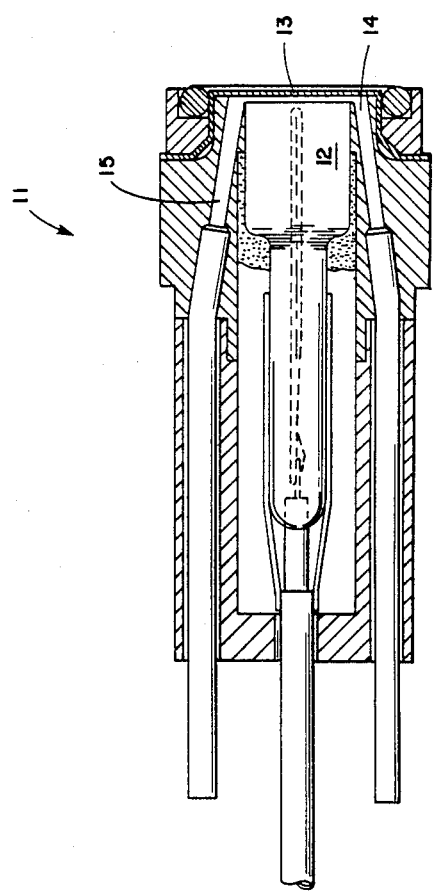
FIG. 1 illustrates an ion-sensing electrode used with the present invention.

The above-mentioned U.S. Pat. Nos. 4,003,705 and 4,170,523 are incorporated herein by reference and made a part of this specification. FIG. 1 illustrates an ion-sensing electrode and is the same as FIG. 4 of U.S. Pat. No. 4,003,705. Referring to FIG. 1, elements essential to this application will be referred to and have been renumbered for ease of illustration. However, the reference numerals from U.S. Pat. No. 4,003,705 will be placed in parentheses behind the new reference numerals to aid in understanding the operation of the apparatus. That is, a complete understanding of the operation of the apparatus of FIG. 1 may be had by reference to the description contained in U.S. Pat. No. 4,003,705.

Referring to FIG. 1, a sensing element 11 (30) includes an ion-sensing electrode 12 (92) and an ion-permeable membrane 13 (108). A passage 14 (114) and a passage 15 (116) allow an electrolyte solution to be pumped between electrode 12 and membrane 13.

Figure 2:
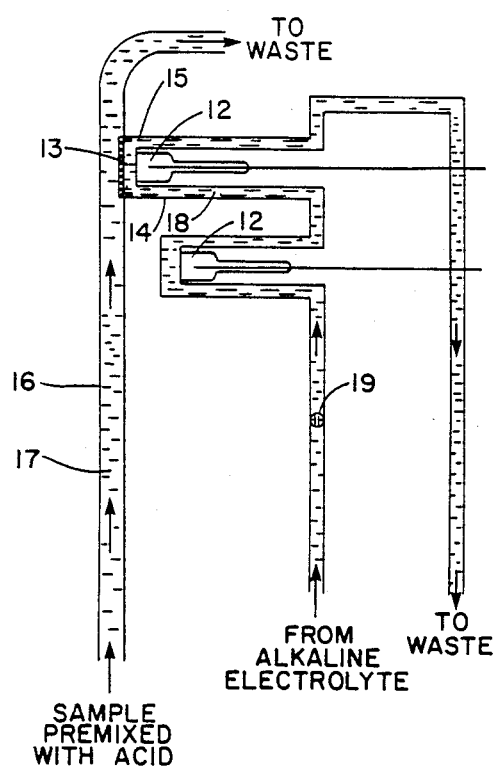
FIG. 2 is a diagram of the apparatus for measuring ionic concentrations utilizing the present invention.

Referring to FIG. 2, a flow cell 16 contains the sample substance premixed with acid to produce substance 17 which is to be measured. Electrode 12 and membrane 13 are positioned adjacent flow cell 16. Passages 14 and 15 allow an electrolyte solution 18 to be pumped between electrode 12 and membrane 13. The flow of electrolyte 18 is controlled by a valve 19. Sample substance 17 contacts membrane 13.

Mode of Operation

Referring to FIG. 2, premixed sample substance 17 is pumped into flow cell 16 and stopped adjacent member 13 such that sample substance 17 contacts membrane 13. Carbon dioxide ($CO_2$) gas, released from sample substance 17, diffuses through membrane 13 to react with the electrolyte solution 18 as described in the incorporated U.S. patents. The partial pressure of carbon dioxide in the internal reference solution in flow cell 16 before the sample substance 17 is pumped into flow cell 16 is not equal to that of the electrolyte solution 18. That is, unlike the situation described in the above referenced U.S. Patents, there is a continual diffusion of $CO_2$ gas through membrane 13. The quantity of $CO_2$ gas released by the internal reference solution is known. Erroneous measurements of the carbon dioxide gas would result if a measurement were immediately taken upon stopping sample substance 17 adjacent membrane 13. That is, the carbon dioxide released from the reference solution is constantly being measured by the electrode and is different from the amount of carbon dioxide released by the sample substance.

In order to overcome the above problem, after the premixed sample is in place electrolyte solution is pumped between electrode 12 and membrane 13 at a rate sufficient to remove the carbon dioxide gas faster than it is diffusing through the membrane. The rate of carbon dioxide diffusion is very slow. If the flow of electrolyte solution 18 is suddenly stopped, preferably by means of valve 19, the reaction of the gas diffusing through the membrane with the electrolyte solution 18 is initiated reproducibly and the rate of reaction is directly proportional to the concentration of carbon dioxide gas. Thus, a measurement may be taken almost immediately upon stopping of the pumping of electrolyte solution 18. In practice, measurements have been taken in as short a time as five seconds.

While the invention has been disclosed with respect to a preferred embodiment thereof, it is not to be so limited as changes and modifications may occur which are within the full intended scope of the invention as defined by the appended claims. For example, while the invention has been disclosed with respect to a system for measuring carbon dioxide gas as the substance of interest, the method may be employed with any sensing element utilizing an electrode, a membrane, and an electrolyte solution therebetween. The method may also be employed to obtain more than one reading from a given sample by pumping and stopping the renewable electrolyte again with the sample remaining in place. The method could also be used to monitor a continually flowing stream where the concentration of the gas or ion of interest may be continually changing. A gradient could thus be generated showing the change over time.

What is claimed is:

1. A method for measuring the concentration of a substance in a sample liquid, said method utilizing an ion-sensing electrode including a permeable membrane spaced from said electrode, said space between said membrane and said electrode containing an electrolyte solution, said method comprising the steps of:

premixing the sample liquid with a reagent to release said substance prior to contact with the permeable membrane;

contacting said permeable membrane with said sample liquid;

circulating said electrolyte solution through said space at a rate greater than said substance diffuses through said membrane;

stopping said circulating electrolyte solution; and measuring said concentration.

2. Method of claim 1 wherein said substance is carbon dioxide.

3. Method of claim 1 wherein said electrolyte includes a bicarbonate ion.

4. Method of claim 1 wherein said electrode is a pH electrode.

5. Method of claim 1 wherein said step of contacting includes stopping said sample substance adjacent said membrane.

* * * * *